(12) United States Patent
Carminati et al.

(10) Patent No.: US 7,683,032 B2
(45) Date of Patent: Mar. 23, 2010

(54) DEGLYCOSYLATED AND DESIALIDATED LONG PENTRAXIN PTX3

(75) Inventors: Paolo Carminati, Milan (IT); Rita De Santis, Pomezia (IT); Antonio Inforzato, Calvi Risorta-Petrulo (IT); Giovanni Salvatori, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 154 days.

(21) Appl. No.: 11/575,346

(22) PCT Filed: Sep. 28, 2005

(86) PCT No.: PCT/EP2005/054860

§ 371 (c)(1),
(2), (4) Date: Jun. 20, 2007

(87) PCT Pub. No.: WO2006/037744

PCT Pub. Date: Apr. 13, 2006

(65) Prior Publication Data

US 2007/0249021 A1 Oct. 25, 2007

(30) Foreign Application Priority Data

Oct. 8, 2004 (IT) .......................... RM2004A0489

(51) Int. Cl.
 *C07K 14/00* (2006.01)
 *A61K 38/00* (2006.01)
(52) U.S. Cl. ....................................... 514/12; 530/350
(58) Field of Classification Search ........................ None
 See application file for complete search history.

(56) References Cited

U.S. PATENT DOCUMENTS

| | | | |
|---|---|---|---|
| 2004/0198655 A1* | 10/2004 | Mantovani | 514/12 |
| 2005/0043230 A1* | 2/2005 | Presta et al. | 514/12 |
| 2008/0026997 A1* | 1/2008 | Carminati et al. | 514/12 |

OTHER PUBLICATIONS

Bowie et al., Deciphering the Message in Protein Sequences: Tolerance to Amino Acid Substitutions. Science. 1990. vol. 247, pp. 1306-1310.*
Wells, J.A., Additivity of Mutational Effects in Proteins. Biochemistry. 1990. vol. 29, No. 37, pp. 8509-8517.*
Barbara Bottazzi, et al. Multimer Formation and Ligand Regognition . . . , The Journal of Biological Chemistry, vol. 272, No. 52, pp. 32817-32823, 1997.
Alma J. Nauta, Biochemical and Functional Characterization of the Interaction . . . , Eur. J. Immunol., vol. 33, pp. 465-473, 2003.
Hideaki Hamazaki, Structure and Significance of n-Linked Sugar Unit . . . , Biochimica et Biophysica Acta., vol. 1037, pp. 435-438, 1990.
Janya Siripont, et al., Receptor-Mediated Binding of the Acute-Phase . . . , Cellular Immunology, vol. 117, pp. 239-252, 1988.
Glenys A. Tennent, et al., Glycobiology of the Pentraxins, Biochemical Society Transactions, vol. 22, No. 1, pp. 74-79, 1994.

* cited by examiner

*Primary Examiner*—Suzanne M. Noakes
(74) *Attorney, Agent, or Firm*—Lucas & Mercanti, LLP

(57) ABSTRACT

Deglycosylated long pentraxin PTX3 and desialidated long pentraxin PTX3 are disclosed, as well as processes for their preparation, pharmacological compositions containing them, and their use for the preparation of a medicament for the treatment of diseases in which the use of the long pentraxin PTX is indicated, particularly infectious and inflammatory diseases and female fertility disorders. These proteins are endowed with therapeutic activity superior to that of glycosylated pentraxin.

25 Claims, 5 Drawing Sheets

Legend:

MW = molecular weight

1 = glycosylated PTX3

2 = PTX3 deglycosylated with Endoglycosidase F3

Legend:

MW = molecular weights

1 = glycosylated PTX3

2 = PTX3 desialidated with Sialidase A

LEGEND to Figure 3 A:   Assay of PTX3 binding to C1q.

- Endo F3: PTX3 deglycosylated with Endo F3;

- Endo F3 BSA: bovine serum albumin treated with Endo F3;

- External PBS: unmodified PTX3;

- External PBS BSA: bovine serum albumin not subjected to treatment with Endo F3.

LEGEND to Figure 3B: Assay of PTX3 binding to C1q.

- Asialo PTX3: desialidated PTX3;

- External: unmodified PTX3;

- BSA Internal: bovine serum albumin treated with Sialidase;

- BSA External: bovine serum albumin not treated with Sialidase.

LEGEND to Figure 4: Assay of complement activation measured as C4 deposition.

- hu PTX3 old: unmodified PTX3;

- huPTX3 sialidase: desialidated PTX3;

- huPTX3 int ctrl: PTX3 treated with the same buffers and in the same temperature conditions as desialidated PTX3, but not treated with Sialidase A..

DEGLYCOSYLATED AND DESIALIDATED LONG PENTRAXIN PTX3

The present invention relates to partially or totally deglycosylated long pentraxin PTX3.

In particular, the present invention relates to deglycosylated long pentraxin PTX3 and desialidated long pentraxin PTX3, their analogues and derivatives, processes for their preparation, pharmaceutical compositions containing these substances, and their use for the preparation of a medicament for the treatment of diseases in which the use of long pentraxin PTX3 is indicated, particularly infectious diseases, inflammatory diseases, including autoimmune diseases and diseases caused by tissue infarct, bone and cartilage diseases, as well as for the treatment of female fertility disorders and autologous vaccines for the treatment of tumours.

BACKGROUND TO THE INVENTION

Long pentraxin PTX3 is identified by differential screening from a cDNA phage library made up of human endothelial cells (HUVEC) submitted to treatment with IL1β (Breviario, et al., 1992, *J. Biol. Chem.*, 267: 22190-22197). Its nucleotide sequence is disclosed in the NCBI database under access number X63613. The cDNA of PTX3 codes for a protein of 381 amino acid residues characterised by a signal peptide for the secretion (residues 1-17), by an N-terminal domain (residues 18-178) and by a C-terminal domain (residues 179-381). The gene of human long pentraxin PTX3 maps on chromosome 3 in the q25.2 region and is characterised by 3 exons located on 6.72 kb of genomic DNA.

Recombinant PTX3, purified from the supernatant of CHO cells stably infected with the plasmid vector pSG5h-PTX3 containing the human cDNA of PTX3, analysed by SDS-PAGE in reducing conditions, presents an apparent molecular weight of 45 kDa (Bottazzi, et al., *J. Biol. Chem.*, 1997; 272: 32817-32823). Its amino acid sequence shows a potential glycosylation site at residue 220. The treatment of PTX3 with N-glycosidase F leads to the reduction of its molecular weight to approximately 42 kDa (estimated by SDS-PAGE) in agreement with the value calculated on the basis of the amino acid sequence alone.

This result confirms that PTX3 is N-glycosylated with a sugar contribution amounting to approximately 12% of the molecular weight. Analysis of the protein analysed by SDS-PAGE in non-reducing conditions yielded a molecular weight of approximately 450 kDa (Bottazzi, et al., *J. Biol. Chem.*, 1997; 272: 32817-32823). These results clearly indicate that PTX3 is mainly organised in a decameric structure through the formation of intermolecular disulphide bridges between the cysteine residues of the individual monomers.

However, the deglycoslation protocol proposed in the above-mentioned paper does not permit the preparation of a functionally active PTX3, in view of the fact that, for this to be done, both denaturation and reduction of the disulphide bridges of the protein are necessary.

The protein obtained according to Bottazzi et al.'s method cannot be used as a medicament, having lost its functional characteristics. No use of the deglycosylated pentraxin is, however, suggested.

The present invention solves the problem by providing functionally active deglycosylated pentraxin PTX3.

For a review of the pentraxins, see H. Gewurz, et al., *Current Opinion in Immunology*, 1995, 7:54-64.

Previous uses of PTX3 are well known.

International patent application WO 99/32516, filed in the name of the present applicant, discloses long pentraxin PTX3 and its use for the therapy of infectious or inflammatory diseases or tumours.

WO 02/38169 discloses the use of long pentraxin PTX3 for the preparation of a medicament useful for the treatment of diseases associated with abnormal activation of growth factor FGF-2.

The treatment of autoimmune diseases by means of the use of long pentraxin PTX3 is disclosed in WO 02/36151.

WO 03/011326 discloses the use of long pentraxin PTX3 for the treatment of female infertility.

WO 03/084561 discloses the use of long pentraxin PTX3 for the preparation of a medicament for the treatment of tumours associated with abnormal activation of growth factor FGF-8.

WO 03/072603 discloses the use of long pentraxin PTX3 for the preparation of autologous vaccines for the treatment of tumours.

PTX3 shares with the short pentraxins CRP and SAP the ability to bind C1q, a component of the complement system. The binding of PTX3 to C1q is saturated with a $K_d$ of $7.4 \times 10^{-8}$ M. Kinetic studies of the bimolecular interaction between PTX3 and C1q carried out using the BIAcore have made it possible to measure a $K_{on}$ of $2.4 \times 10^5$ M$^{-1}$ s$^{-1}$ and a $K_{off}$ of $4 \times 10^{-4}$ s$^{-1}$ (Bottazzi, et al., *J. Biol. Chem.*, 1997; 272: 32817-32823).

The comparative analysis of the sequence homology between PTX3 and short pentraxins has revealed a substantial homology of the C-terminal domain of PTX3 with the entire sequence of CRP and SAP (Breviario, et al., 1992, *J. Biol. Chem.*, 267: 22190-22197). Both CRP and SAP compete for the binding of C1q to PTX3, suggesting that the pentraxins recognise the same region on C1q and that the C-terminal domain of PTX3 is the binding site for C1q. In-vitro studies have shown that PTX3 activates the classic complement pathway.

Experimental and clinical evidence shows that functional abnormalities of complement are associated with a greater proneness to infection by pathogens, thus demonstrating an essential function of this innate immune system in protection against infections (Roos, et al., 2002, *Immunobiol.*, 205: 595-609). In the medical field, then, there is a strongly perceived need for drugs capable of boosting and amplifying the immune response to complement-mediated microbial infections.

Moreover, experts in the field are looking for drugs which are increasingly active and capable of acting in synergy with other drugs.

DESCRIPTION OF THE INVENTION

It has now surprisingly been found that the removal of sialic acid from the end of the glycoside chain or the complete removal of the glycoside group of PTX3 produces a highly significant increase in the ability of this protein to activate the classic complement pathway.

It has also been found that PTX3 devoid of sialic acid (desialidated) and deglycosylated PTX3 are useful agents for the prevention or treatment of infectious diseases, particularly of fungal, bacterial or viral infections at a dose lower than that used with unmodified PTX3. It has also been found that PTX3 devoid of sialic acid (desialidated) and deglycosylated PTX3 are useful in the prevention or treatment of diseases already treated with naturally occurring PTX3, particularly inflammatory diseases, including autoimmune diseases, tumours, diseases due to abnormal activation of growth factor FGF-2, female fertility disorders, bone and cartilage diseases, and for the preparation of autologous vaccines for the treatment of tumours.

It has also been found that both deglycosylated and desialidated PTX3 can be used to advantage for preventive vaccination against pathogens, showing a tendency to favour an adaptive-type immune response.

One object of the present invention then is deglycosylated long pentraxin PTX3, or one of its functionally active analogues or derivatives.

Another object of the present invention is desialidated long pentraxin PTX3, or one of its functionally active analogues or derivatives. Another object of the present invention comprises processes for the preparation of the above-mentioned proteins.

Another object of the present invention comprises pharmaceutical compositions containing deglycosylated or desialidated pentraxin PTX3, or one of their functional analogues or derivatives, as the active ingredient and at least one pharmaceutically acceptable excipient and/or vehicle.

A further object of the present invention is the use of deglycosylated or desialidated long PTX3, or one of their functional analogues or derivatives, for the preparation of a medicament capable of binding complement, particularly for the treatment of infectious diseases of bacterial, fungal, protozoan or viral origin.

A further object of the present invention is the use of deglycosylated or desialidated long PTX3 as adjuvants for preventive vaccination against pathogens and antigens.

BRIEF DESCRIPTION OF THE DRAWINGS

The invention will now be disclosed in detail, also with the aid of examples and figures, where.

DETAILED DESCRIPTION OF THE INVENTION

Figure 1:
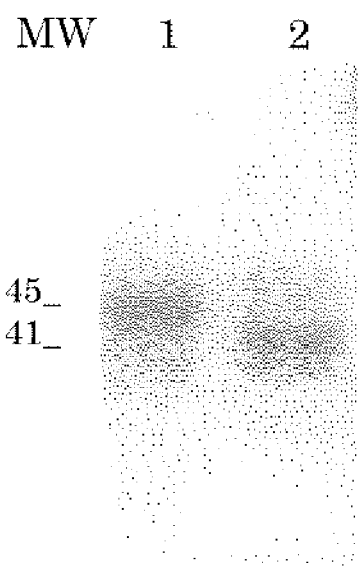
FIG. 1 shows the electrophoretic mobility of pentraxin deglycosylated with Endoglycosidase F3.

What is meant by "deglycosylated or desialidated long pentraxin PTX3" is any PTX3, regardless of its natural (human or non-human) or recombinant origin. These pentraxins PTX3 are described in the literature: see, for example, the patent references of the present applicant: and the bibliographical references cited therein.

What is meant by derivative or analogue of "deglycosylated or desialidated long pentraxin PTX3" is either a functional analogue of said pentraxin bearing at least one mutation, and which retains the ability to bind and activate C1q, or a peptidic or peptidomimetic derivative capable of simulating linear or conformational domains of PTX3 and which retains the functional ability to bind and activate C1q.

What is meant by functionally active deglycosylated or desialidated long pentraxin PTX3 are those products retaining the biological ability of naturally occurring pentraxin, particularly its complement binding ability.

For a description of derivatives or analogues, see WO 03/38151.

The deglycosylated or desialidated long pentraxin PTX3 preferred is the human one, whose sequence is disclosed in WO 99/32516.

The process for the preparation of deglycosylated pentraxin comprises the deglycosylation of long pentraxin PTX3.

The starting long pentraxin PTX3 is a known protein, and the methods for obtaining it are also known.

Any protein deglycosylation process is suitable for the purpose, with on condition that it should not induce any loss or substantial alteration of pentraxin activity.

In one preferred embodiment of the invention, the process comprises treating long pentraxin PTX3 with the endoglycosidase EndoF3.

Alternatively, the present invention also provides a process for the preparation of deglycosylated long pentraxin PTX3 which comprises the cultivation of cells expressing long pentraxin PTX3 in the presence of a glycosylation inhibitor. One preferred inhibitor is tunicamycin. Cells expressing pentraxin are known in the field and can be obtained easily on the basis of the general knowledge of the expert in the art. Examples of such cells are cells transfected with the cDNA of human PTX3, such as CHO (Chinese Hamster Ovary) cells.

Similarly, any protein desialidation process is suitable for the purpose, with the proviso that the process should not induce any loss or substantial alteration of pentraxin activity. A possible example is the use of desialidase A.

Similarly, any protein engineering process suitable for the purpose, such as, for example, the production if recombinant PTX3 mutagenised by destruction of the glycosylation sites, can be used, with the proviso that the process should not induce any loss or substantial alteration of pentraxin activity.

The present invention provides the use of deglycosylated and desialidated long pentraxin PTX3 or their functional analogues or derivatives as a medicament.

What is meant by infectious disease is a disease caused by bacterial, fungal, protozoan or viral infections.

Examples of autoimmune diseases are systemic lupus erythematosus (SLE), multiple sclerosis (MS), arthritis, diabetes, thyroiditis, haemolytic anaemia, atrophic orchitis, Goodpasture's disease, autoimmune retinopathy, autoimmune thrombocytopenia, myasthenia gravis, primary biliary cirrhosis, aggressive chronic hepatitis, ulcerative colitis, dermatitis, chronic glomerulonephritis, Sjögren's syndrome, Reiter's syndrome, myositis, systemic sclerosis and polyarthritis.

What is meant by tissue infarct is cardiac or cerebral infarction

What is meant by female fertility treatment is any use of deglycosylated or desialidated PTX3 to improve the fertility of women requiring such treatment.

In particular, the present invention provides the use of deglycosylated or desialidated long pentraxin PTX3 for the preparation of a medicament capable of binding complement.

One preferred application relates to a medicament for the prevention or treatment of infectious diseases.

In particular, the infectious agent in said diseases is a bacterium, fungus, protozoon or virus.

One preferred embodiment of the invention relates to the fungus *Aspergillus*, and particularly to *Aspergillus fumigatus*.

Another aspect of the invention is a medicament for the treatment of fungal infections that comprises a combination of deglycosylated or desialidated long pentraxin PTX3 and an antifungal, preferably of the amphotericin class, such as amphotericin B, particularly as deoxycholate or in a liposomal formulation. The formulation is a further object of the present invention.

It has also been found that deglycosylated and/or desialidated long pentraxin PTX3 is useful as an adjuvant for preventive vaccination against selected pathogens or antigens, and this constitutes a further object of the present invention.

The vaccine containing the deglycosylated and/or desialidated protein as an adjuvant can be used to advantage against a pathogenic agent, such as a bacterium, fungus, protozoon or virus, or one of their antigens.

In one preferred embodiment of the invention, the pathogenic agent is a fungus, particularly Aspergillus, and more particularly, *Aspergillus fumigatus*, as well as one of its antigens.

In addition to containing deglycosylidated and/or desialidated long pentraxin PTX3 as an adjuvant, the vaccine according to the present invention is prepared with entirely conventional methods known to the skilled person with experience in the field, and therefore requires no further explanation.

Given here below are a number of examples further illustrating the invention.

Example 1

Preparation of Deglycosylated PTX3

PTX3, purified from the supernatant of CHO cells stably transfected with the plasmid vector pSG5hPTX3 containing the human cDNA of PTX3 (as disclosed in Bottazzi, et al., *J. Biol. Chem.* 1997; 272: 32817-32823), was treated with the endoglycosylidase EndoF3 for the removal of the entire glycoside chain minus the N-acetylglycosamine residue bound to asparagin 220.

In particular, PTX3 was incubated with Endoglycosidase F3 known for its selective hydrolysation of the glycoside β bond (1□4) between the two GlcNac residues present in the nucleus of oligosaccharides of the N-linked bi- and triantennary complex type. Endoglycosidase F3 manifests its maximum catalytic activity at acid pH values. On the basis of the solubility characteristics of PTX3 the use of a phosphate buffer at pH 5.5 was optimised. The Endoglycosidase F3 used in the experiment comes from the cDNA of *Chryseobacterium (Flavobacterium) merningosepticum* expressed in *E. coli* as recombinant protein (Sigma Aldrich code E2264). The enzymatic hydrolysis of the sugars of the purified PTX3 was evaluated by means of its electrophoretic mobility variation in SDS-PAGE (see FIG. 1). Approximately 10 μg of PTX3 in 7 μl of sterile water were added with 2 μl of phosphate buffer at pH 5.5 (5×) ($NaH_2PO_4$ 250 mM) and with 1 μl of Endoglycosidase F3 taken from the mother solution (Sigma Aldrich). The mixture was incubated at 37° C. for 12 hours. The reaction is scalable up to 1 mg of PTX3.

The deglycosylated PTX3 thus obtained was purified by gel filtration chromatography (Superose 6 PHARMACIA) for the purposes of removing the glycoside enzymes and the sugars. SDS-PAGE gel filtration was done as disclosed by Bottazzi et al., *J. Biol. Chem.* 1997; 272: 32817-32823

Example 2

Preparation of Deglycosylated PTX3

The PTX3-producing CHO cells described in Example 1 were treated with a glycosylation inhibitor of the proteins, such as, for instance, tunicamycin (Sigma Aldrich).

The deglycosylated PTX3 thus obtained was purified as disclosed in Bottazzi et al. *J. Biol Chem* 1997; 272: 32817-32823.

Any other known method for the deglycosylation of proteins or for the production of deglycosylated proteins that does not alter their functional capability is suitable for the purposes of the present invention.

Example 3

Preparation of Desialidated PTX3

PTX3 purified from the supernatant of CHO stably transfected with the plasmid vector pSG5h-PTX3 containing the human cDNA of PTX3 was used.

Figure 2:
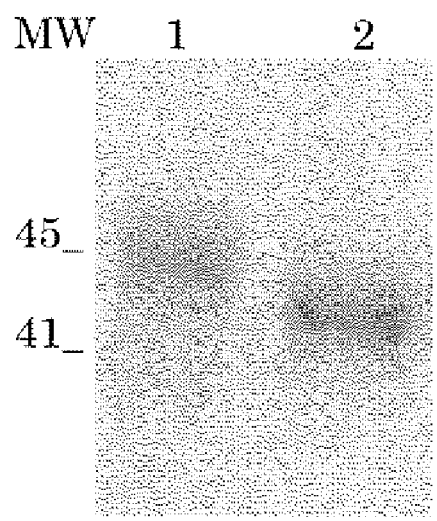
FIG. 2 shows the electrophoretic mobility of pentraxin desialidated with Sialidase A.

PTX3 was treated with Sialidase A. The Sialidase A [α(2→3,6,8,9) neuraminidase] used came from the cDNA of *Arthrobacter ureafaciens* expressed in *E. coli* as recombinant protein (SIGMA Aldrich code N8271). The desialidation of PTX3 was also evaluated by means of analysis of its electrophoretic mobility variation by SDS-PAGE (see FIG. 2).

The desialidated PTX3 thus obtained was purified by gel filtration chromatography (Superose 6 PHARMACIA) for the purposes of removing the glycoside enzymes and the sugars.

Any other known method for the desialidation of proteins or for the production of desialidated proteins that does not alter their functional capability is suitable for the purposes of the present invention.

Example 4

Assay of Deglycosylated PTX3 Binding to C1q

Maxisorp (NUNC) plates were treated with 0.5 μg/ml of C1q (CALBIOCHEM) for the purposes of adsorbing the protein on the inner surface of the wells. After subsequent washings in phosphate buffer (GIBCO) the wells were incubated in phosphate buffer for 1 hour with deglycosylated PTX3 at the dosages indicated in FIG. 3.

The relative amounts of PTX3 bound to C1q were determined using a biotinylated anti-PTX3 polyclonal antibody, Streptavidin-HRP (PHARMACIA) and staining with TMB.

Figure 3A:
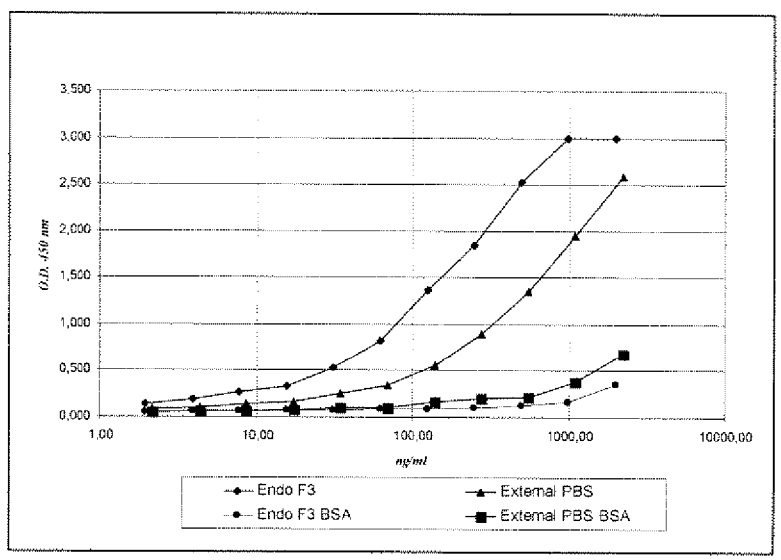
FIGS. 3A and 3B illustrate the binding assay of deglycosylated and desialidated long pentraxin, respectively, to C1q.
Figure 3:
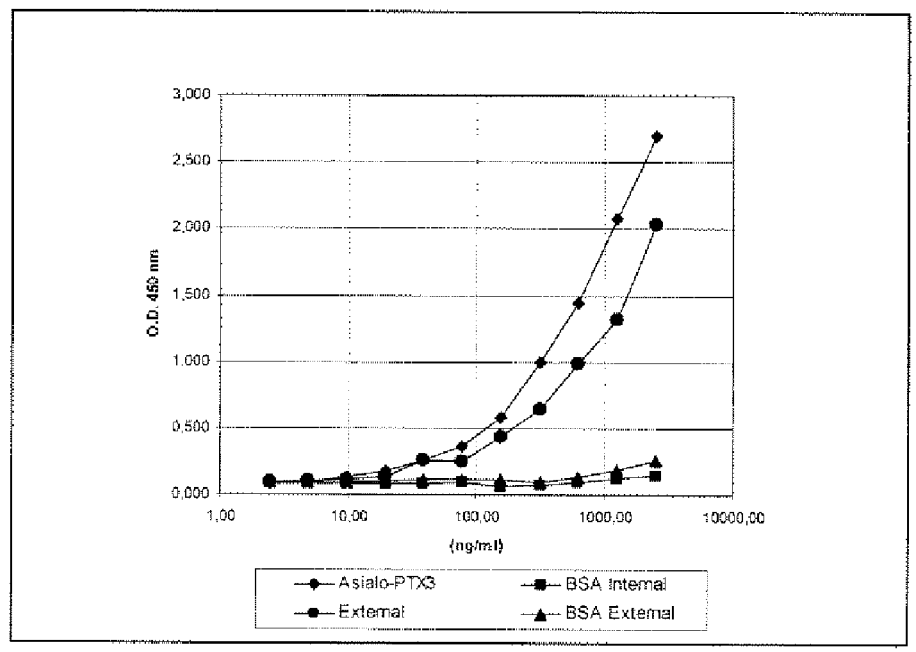

The deglycosylated PTX3 showed binding to C1q which was approximately 4-fold greater than that of PTX3 not treated with glycosidase (FIG. 3A).

Example 5

Assay of Desialidated PTX3 Binding to C1q

The assay of Desialidated PTX3 binding to al C1q was performed in the same experimental conditions described in the previous example and at the dosages indicated in FIG. 3B.

In this case, too, the desialidated PTX3 showed binding to C1q which was approximately 2-fold greater than that of PTX3 not treated with desialidase (FIG. 3B).

Example 6

Evaluation of the Ability of Desialidated PTX3 to Activate the Classic Complement Pathway Desialidated PTX3 was adsorbed on 96-well Maxisorp plates at a concentration of 5 μg/ml (carbonate buffer 0.1 M pH 9.6). Subsequently, the wells were treated with human serum (NHS) as a source of complement at different dilution percentages. The amount of C4 deposited on the plates as a result of complement activation was measured using the anti-C4 antibody (C4-4°) as disclosed by Nauta et al. in *Eur. J. Immunology,* 2003, 33: 465-473.

Figure 4:
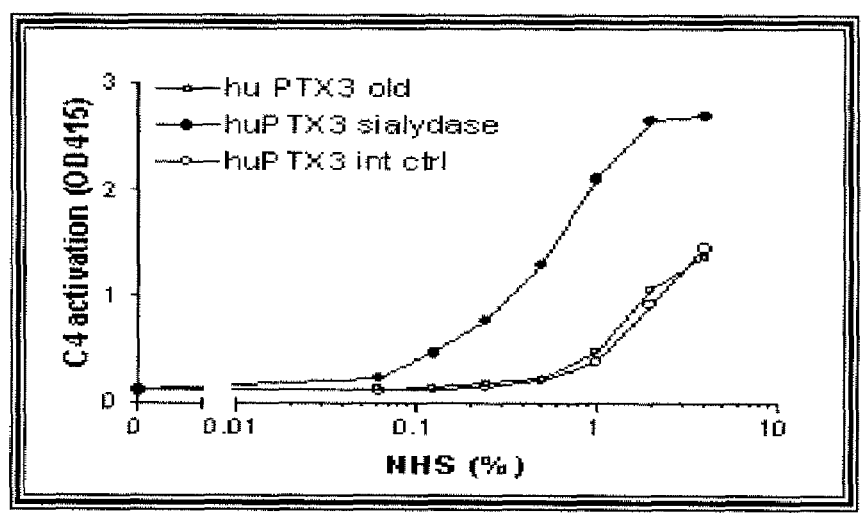
FIG. 4 illustrates the complement activation assay.

The amount of C4 deposited on the platelet adsorbed with desialidated PTX3 was approximately 8-fold greater than that of the platelet adsorbed with the control PTX3 (FIG. 4). The result shows that desialidated PTX3 is more active than unmodified PTX3 in its complement activation ability.

Example 7

Evaluation of the Ability of Deglycosylated PTX3 to Activate the Classic Complement Pathway Deglycosylated PTX3 was tested in the same experimental conditions used for desialidated PTX3 described in Example 6.

The results obtained were comparable to those obtained with desialidated PTX3.

As regards the aspects relating to industrial applicability, deglycosylated or desialidated PTX3, or their peptidic or peptidomimetic derivatives will be in the form of pharmaceutical compositions in which the active ingredients are solubilised and/or vehicled by pharmaceutically acceptable excipients and/or vehicles, such as sterile water, carboxymethylcellulose or other excipients known to experts in the art.

Examples of pharmaceutical compositions that can be used for deglycosylated or desialidated PTX3 are the same as those disclosed for long pentraxin PTX3 (in WO 99/32516).

Further examples of pharmaceutical compositions are those which allow oral or parenteral administration via the intravenous, intramuscular, subcutaneous, transdermal, rectal or vaginal routes. Pharmaceutical compositions suitable for the purpose are tablets and rigid or soft capsules, suppositories, ovules, powders, solutions, suspensions, syrups, or solid forms for the preparation of extempore liquids. Compositions for parenteral administration are, for example, all the intramuscular, intravenous and subcutaneous injectable forms, in the form of solutions, suspensions or emulsions. Liposomal forms should also be mentioned. Also included are forms for the controlled release of the active ingredient, whether as oral administration forms, tablets coated with appropriate layers, microencapsulated powders, cyclodextrin complexes, depot forms, e.g. subcutaneous, or as depot injections or implants. Compositions for aerosol administration may constitute a preferred administration form.

The daily dose will depend on the judgement of the primary care physician on the basis of the patient's weight, age and general condition.

It should be noted that the preparation of said pharmaceutical compositions, including the slow-release forms, can be done using the common techniques and instruments with which pharmacists and experts in pharmaceutical technology are very familiar. As a reference, the expert in the field can refer to the usual literature, such as, for example, the latest edition of *Remington's Pharmaceutical Sciences Handbook*, Mack Pub. N.Y. As regards the vaccines, the reader is referred to the specific literature, e.g. international patent applications WO 03/011903 and PCT/IT03/00162.

The invention claimed is:

1. Functionally active deglycosylated long pentraxin PTX3.

2. Long pentraxin PTX3 according to claim 1, which is of natural human or nonhuman, or recombinant origin.

3. Process for the preparation of deglycosylated long pentraxin PTX3 according to claim 1, comprising the deglycosylation of long pentraxin PTX3.

4. Process according to claim 3, in which said deglycosylation is carried out with endoglycosidase EndoF3.

5. Process for the preparation of deglycosylated long pentraxin PTX3 according to claim 1, comprising the cultivation of cells expressing long pentraxin PTX3 in the presence of a glycosylation inhibitor.

6. Process according to claim 5 in which said inhibitor is tunicamycin.

7. Process according to claim 3, in which said deglycosylation is obtained by mutagenising the glycosylation site of PTX3.

8. Process according to claim 3, in which the deglycosylated long pentraxin PTX3 is purified.

9. Process according to claim 8, in which said purification is performed by gel filtration chromatography.

10. Pharmaceutical composition containing deglycosylated long pentraxin PTX3 according to claim 1 derivatives in a mixture with at least one pharmaceutically acceptable vehicle or excipient.

11. A method for the treatment of infectious diseases comprising administering a medicament containing deglycosylated long pentraxin PTX3 according to claim 1.

12. A method for the treatment of inflammatory diseases, including autoimmune diseases, tumours, diseases due to abnormal activation of growth factor FGF-2, female fertility disorders, tissue infarct and bone or cartilage diseases comprising administering a medicament containing deglycosylated long pentraxin PTX3 according to claim 1.

13. The method according to claim 12, in which said autoimmune disease is selected from the group consisting of systemic lupus erythematosus (SLE), multiple sclerosis (MS), arthritis, diabetes, thyroiditis, haemolytic anaemia, atrophic orchitis, Goodpasture's disease, autoimmune retinopathy, autoimmune thrombocytopenia, myasthenia gravis, primary biliary cirrhosis, aggressive chronic hepatitis, ulcerative colitis, dermatitis, chronic glomerulonephritis, Sjogren's syndrome, Reiter's syndrome, myositis, systemic sclerosis and polyarthritis.

14. The method according to claim 12, in which said tissue infarct is selected from the group consisting of cardiac and cerebral infarction.

15. The method according to claim 11, in which in said infectious diseases are caused by a bacterium, fungus, protozoon or virus.

16. The method according to claim 15, in which said fungus is an *Aspergillus*.

17. The method according to claim 16, in which said fungus is *Aspergillus fumigatus*.

18. Combination of functionally active deglycosylated long pentraxin PTX3 with an antifungal agent.

19. Combination according to claim 18, in which said antifungal agent belongs to the amphotericin class.

20. Combination according to claim 19, in which said amphotericin is amphotericin B.

21. Pharmaceutical composition containing the combination according to claim 18 in a mixture with a pharmaceutically acceptable vehicle or excipient.

22. A method for the treatment of fungal infections comprising administering the combination according to claim 18.

23. Method according to claim 22, in which the fungus in said infection is an *Aspergillus*.

24. Method according to claim 23, in which said fungus is *Aspergillus fumigatus*.

25. Combination according to claim 20, wherein said amphotericin B is deoxycholate amphotericin B or in liposomal formulation.

* * * * *